United States Patent
Heo et al.

(10) Patent No.: US 6,960,265 B2
(45) Date of Patent: Nov. 1, 2005

(54) APPARATUS AND METHOD FOR COLLECTING METALLIC IMPURITY ON A SEMICONDUCTOR WAFER

(75) Inventors: Yong-Woo Heo, Yongin (KR); June-Ing Gill, Suwon (KR); Mi-Kyoung Lee, Suwon (KR); Hyun-Gi Cho, Suwon (KR)

(73) Assignee: Samsung Electronics Co., Ltd. (KR)

( * ) Notice: Subject to any disclaimer, the term of this patent is extended or adjusted under 35 U.S.C. 154(b) by 150 days.

(21) Appl. No.: 10/104,094

(22) Filed: Mar. 21, 2002

(65) Prior Publication Data

US 2002/0134406 A1 Sep. 26, 2002

(30) Foreign Application Priority Data

Mar. 21, 2001 (KR) .................................. 10-2001-0014719

(51) Int. Cl.[7] .................................................. B08B 7/04
(52) U.S. Cl. .............................. 134/3; 134/21; 134/26; 134/28; 134/95.1; 134/95.2; 134/104.2; 134/104.4; 134/148; 134/153; 134/157; 134/902
(58) Field of Search ................................ 134/3, 21, 18, 134/26, 28, 95.1, 95.2, 104.2, 104.4, 148, 153, 157, 902; 422/102

(56) References Cited

U.S. PATENT DOCUMENTS

| | | | | |
|---|---|---|---|---|
| 5,001,084 A | * | 3/1991 | Kawai et al. ................ | 438/782 |
| 5,569,328 A | * | 10/1996 | Petvai et al. ................ | 118/696 |
| 6,053,984 A | * | 4/2000 | Petvai et al. ................ | 134/3 |
| 6,182,675 B1 | * | 2/2001 | Naka et al. ................ | 134/61 |
| 6,431,184 B1 | * | 8/2002 | Taniyama ................ | 134/1.3 |
| 6,517,641 B2 | * | 2/2003 | Fernandez ................ | 134/33 |
| 2004/0163670 A1 | * | 8/2004 | Ko et al. ................ | 134/2 |

* cited by examiner

*Primary Examiner*—Zeinab El-Arini
(74) *Attorney, Agent, or Firm*—F. Chau & Associates LLC

(57) ABSTRACT

An apparatus and method for automatically collecting metallic impurities of a semiconductor wafer. In one aspect, an apparatus includes an air tight process chamber including a loading unit for loading the semiconductor wafer and unloading unit for unloading the semiconductor wafer; a vapor phase decomposition unit disposed in the process chamber for decomposing a silicon oxide layer on the semiconductor wafer; and a scanning unit disposed in the process chamber for scanning the semiconductor wafer to collect the metallic impurities. The scanning unit includes a scanning solution bottle for obtaining scanning solution that is used for absorbing metallic impurities on the semiconductor wafer; a scanning arm capable of downward, upward, and rotational movement; and a nozzle coupled to the scanning arm for drawing in scanning solution from the scanning solution bottle, and for forming a droplet of scanning solution that cohers to the nozzle when scanning a semiconductor wafer to collect metallic impurities.

20 Claims, 8 Drawing Sheets

APPARATUS AND METHOD FOR COLLECTING METALLIC IMPURITY ON A SEMICONDUCTOR WAFER

CROSS-REFERENCE TO RELATED APPLICATION

This application claims priority to Korean Patent Application No. 2001-14719 filed on Mar. 21, 2001.

BACKGROUND

1. Technical Field

The present invention relates to an apparatus and method for collecting impurities on a semiconductor wafer and, more particularly, to an automated apparatus and method for scanning a semiconductor wafer to collect metallic impurities on the semiconductor wafer.

2. Description of Related Art

As semiconductor devices become highly integrated, various types of impurities are generated during a semiconductor manufacturing process that settle on a semiconductor wafer. These impurities cause deterioration in the performance of semiconductor devices, as well as lower yields in the manufacturing of semiconductor devices. There is a need therefore for improved methods and devices for removing impurities on semiconductor devices.

One conventional method of analyzing impurities on a semiconductor wafer is as follows. A manufactured semiconductor wafer is selected and then scanned to collect an impurity sample. The impurity sample is then analyzed using an analysis technique such as an atomic absorption spectroscopy (AAS), an induction coupled plasma (ICP) mass spectroscopy, and a total x-ray fluorescent analyzer.

To properly collect the impurities on the semiconductor wafer, a silicon oxide layer that is coated on the surface of the semiconductor wafer is first decomposed using, for example, a VPD (vapor phase decomposition) apparatus.

A conventional VPD apparatus comprises a process chamber, a loading plate for loading the semiconductor wafer into the process chamber, and a container containing a hydrofluoric acid (HF) that is used to decompose a silicon oxide layer of the surface of the semiconductor wafer. When the semiconductor wafer is transferred to the loading plate in the process chamber, the semiconductor wafer rests on the loading plate for a predetermined time period, and the silicon oxide layer is decomposed from the surface of the semiconductor wafer by HF vapors generated in the container. Afterwards, the semiconductor wafer is taken out of the process chamber. A scanning solution is dropped onto the semiconductor wafer and is scanned, thereby collecting the impurity sample manually. The collected impurity sample is analyzed using a technique such as the AAS, the ICP-mass spectroscopy, and the total x-ray fluorescent analyzer.

One disadvantage associated with the above-described conventional method for collecting metallic impurities on the semiconductor wafer is that the scanning process is manually performed and, consequently, the reliability of analyzed data depends on the skill of the person who performs the impurity collection. Another disadvantage is that the semiconductor wafer is scanned in the air and, consequently, alien substances in the air can contaminate the impurity sample. Therefore, it is difficult to precisely analyze the impurity sample.

SUMMARY OF THE INVENTION

To solve the above and other related problems of the prior art, the present invention provides an automated apparatus and method for collecting impurities on a semiconductor wafer, which provides reliable analysis data.

In one aspect of the invention, an apparatus for collecting metallic impurities of a semiconductor wafer comprises: a process chamber comprising a loading unit for loading the semiconductor wafer and unloading unit for unloading the semiconductor wafer; a vapor phase decomposition unit disposed in the process chamber for decomposing a silicon oxide layer on the semiconductor wafer; and a scanning unit disposed in the process chamber for scanning the semiconductor wafer to collect metallic impurities. The scanning unit comprises: a scanning solution bottle for storing scanning solution that is used for absorbing metallic impurities on the semiconductor wafer; a scanning arm capable of upward, downward and rotational movement; and a nozzle for coupling to the scanning arm for drawing in scanning solution from the scanning solution bottle, and for forming a droplet of scanning solution that coheres to the nozzle when scanning the semiconductor wafer to collect metallic impurities.

In another aspect, the apparatus comprises a drying unit for drying the semiconductor wafer.

In yet another aspect of the present invention, the nozzle comprises a coupling portion for coupling to the scanning arm, and an injecting portion for contacting the scanning solurtion to the semiconductor wafer. The bottom surface of the injecting portion comprises a concave-shaped portion.

In another aspect, the scanning arm comprises a nozzle-coupling portion and a nozzle-removing portion. The nozzle-coupling portion is coupled to the coupling portion of the nozzle (using a clip-type connection, for example), and the nozzle-removing portion decouples the nozzle from the scanning arm by pneumatic pressure that is supplied from an air channel in the scanning arm. The scanning arm further comprises a pumping channel for supplying either a pumping force or a suction force so that the scanning solution can be, e.g., drawn into the nozzle by the suction force or emptied from the nozzle into the sampling cup by the pumping force.

In yet another aspect, the scanning unit further comprises: a wafer aligner comprising an alignment hand and a loading plate, wherein the semiconductor wafer is aligned with the loading plate by the alignment hand; a nozzle tray comprising a plurality of nozzle reception grooves for accepting a plurality of nozzles; a sampling cup tray comprising a plurality of sampling cup reception holes for accepting a plurality of sampling cups, wherein the collected metallic impurities are placed in the sampling cup; and a nozzle bottle for disposing used nozzles therein.

In other aspects of the present invention, the scanning solution bottle is arranged on a central portion of the nozzle tray. The loading plate is rotated by a motor. The scanning solution comprises $H_2O$, $H_2O_2$, and HF and the scanning solution preferably comprises a composition ratio of $H_2O:H_2O_2$: HF of about 95:4:1, respectively.

In another aspect of the present invention, an automated method for collecting metallic impurities on the semiconductor wafer comprises the steps of: decomposing a silicon oxide layer on the semiconductor wafer using hydrofluoric acid vapors; drawing scanning solution into a nozzle and forming a droplet of scanning solution that coheres to the nozzle; and scanning the semiconductor wafer by contacting the droplet of scanning solution to the semiconductor wafer to collect metallic impurities. Preferably, the hydrofluoric acid is preheated to a desired temperature. Preferably, the scanning solution is draws into the nozzle so that the level of scanning solution in the nozzle does not contact a nozzle coupling portion of a scanning arm.

In another aspect, the step of scanning comprising positioning the nozzle at a predetermined point using the scanning arm and then rotaing a loading plate holding the semiconducor wafer to rotate the wafer. As the wafer rotates, the nozzle is held at the predetermined point until the semiconductor wafer makes one rotation. Then, the nozzle is moved by the scanning arm inwardly or outwarldy to another predetermined point to continue the scanning. The nozzle is continually positionsed such that there is no overlap of a previoulsy scanned portion of the wafer.

In another aspect, an automated method for collecting metallic impurities on a semiconductor wafer, comprises the steps of: loading a semiconductor wafer in a loading unit; transferring the semiconductor wafer to a vapor phase decomposition device; decomposing a silicon oxide layer on the semiconductor wafer using hydrofluoric acid vapors in the vapor phase decomposition device; transferring the semiconductor wafer to a scanning unit and coupling a nozzle to a scanning arm; drawing scanning solution into the nozzle and forming a droplet of scanning solution on the nozzle; contacting the droplet of scanning solution to the semiconductor wafer to scan the semiconductor wafer and absorb metallic impurities into the scanning solution; and drawing the droplet of scanning solution haivng metallic impurities back into the nozzle and disposing the scanning solution from the nozzle into a sampling cup. In another aspect, the method further comprises transferring the nozzle to a nozzle bottle; decoulping the nozzle into the nozzle bottle; and transferring the semiconductor wafer to a unloading unit.

These and other objects, features and advantages of the invention will become more apparent from the following detailed description of the preferred embodiments made with reference to the accompanying drawings.

BRIEF DESCRIPTION OF THE DRAWINGS

For a more complete understanding of the present invention and the advantages thereof, reference is now made to the following descriptions taken in conjunction with the accompanying drawings, in which similar reference numerals denote similar components, and in which.

DETAILED DESCRIPTION OF PREFFERED EMBODIMENTS

The present invention will now be described more fully with reference to the accompanying drawings, in which preferred embodiments of the invention are shown. Those of ordinary skill in the art can readily envision various embodiments for implementing the present invention and the exemplary embodiments described herein should not be construed as a limitation of the overall scope of the present invention.

Figure 1:
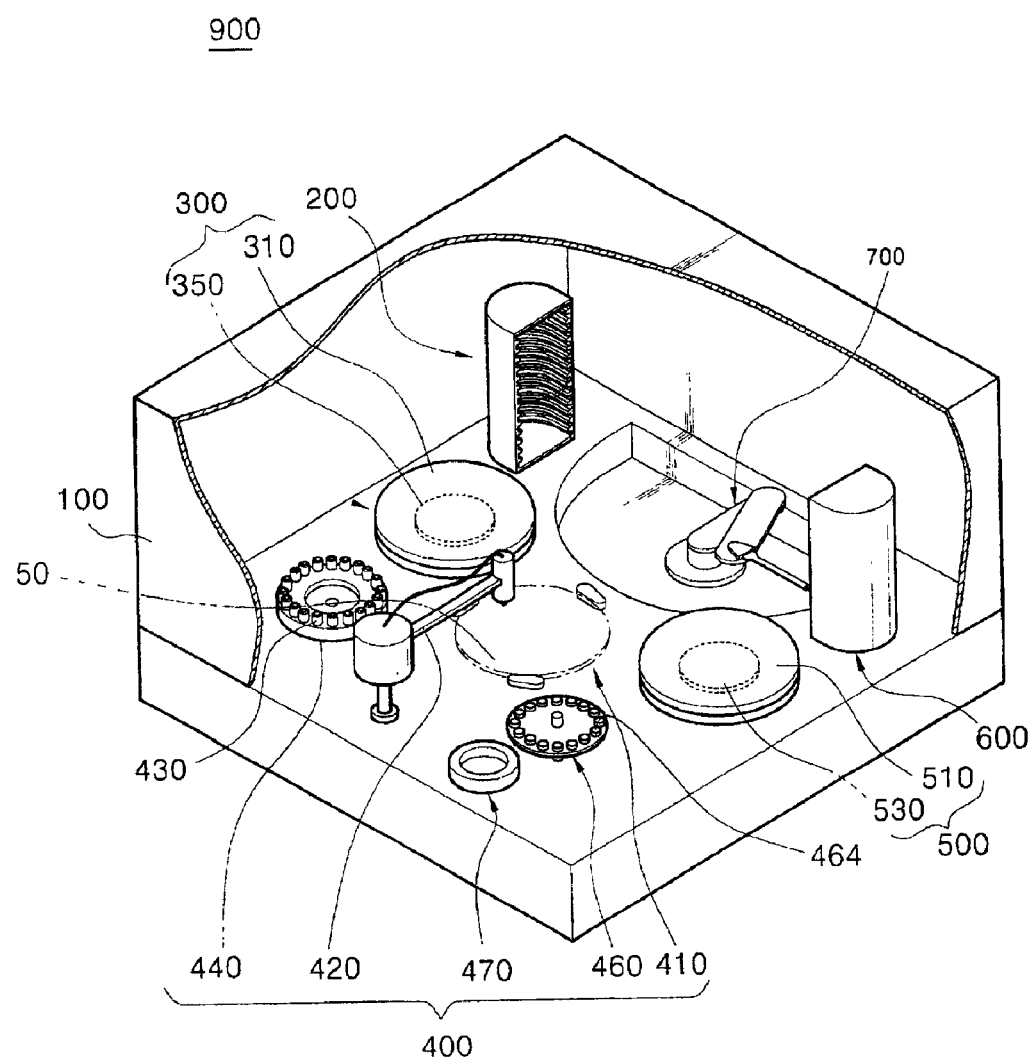
FIG. 1 is a perspective view of a metallic impurity collecting apparatus according to an embodiment of the present invention.
Figure 2:
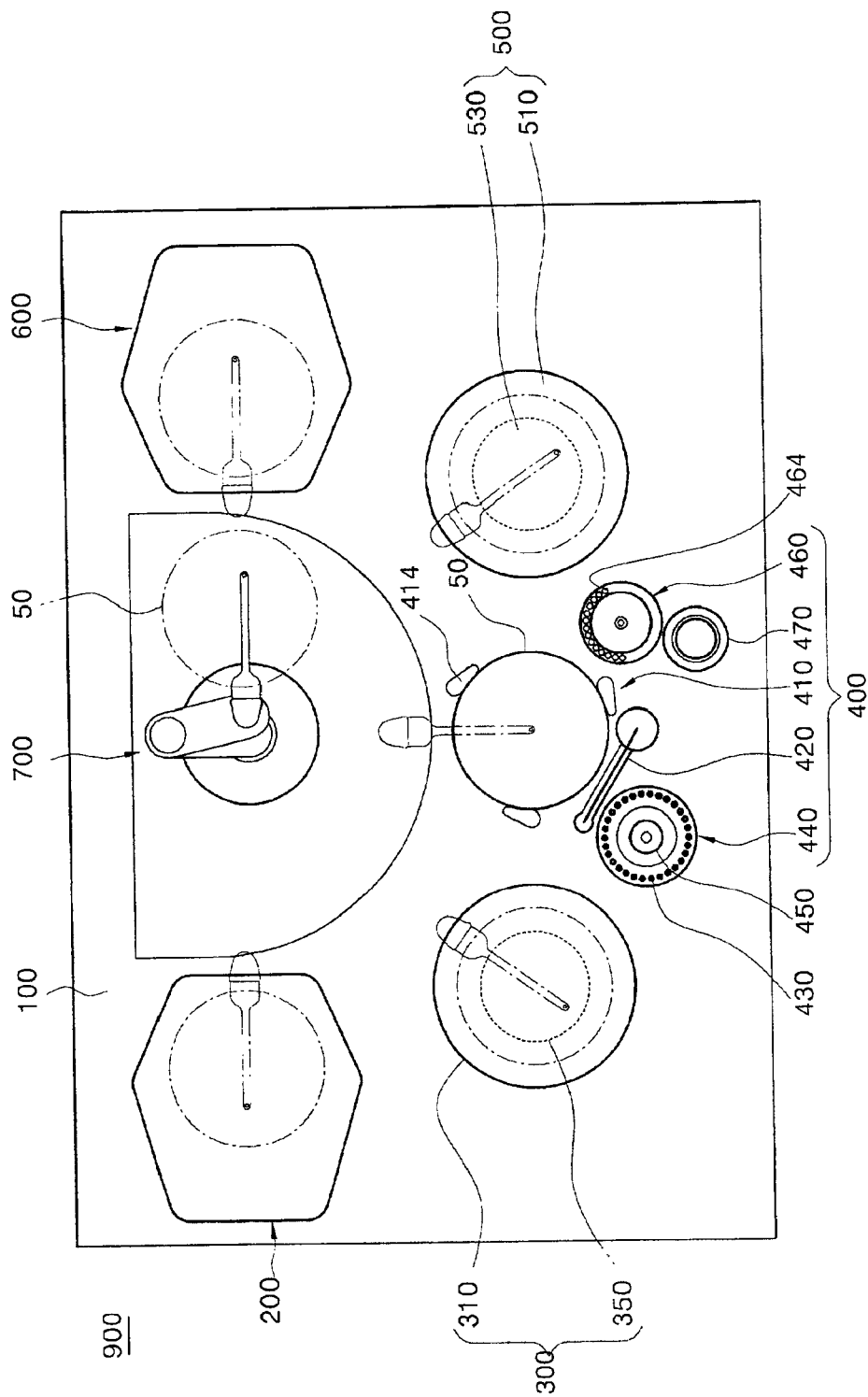
FIG. 2 is a top view of the apparatus of FIG. 1.

FIG. 1 is a perspective view illustrating a metallic impurity collecting apparatus according to a preferred embodiment of the present invention. FIG. 2 is a top view of the metallic impurity collecting apparatus of FIG. 1.

A metallic impurity collecting apparatus 900 according to an embodiment of the present invention comprises a process chamber 100, a transferring robot unit 700, a loading unit 200, a vapor phase decomposition (VPD) 300, a scanning unit 400, a drying unit 500, and an unloading unit 600. The metallic impurity collecting apparatus 900 further comprises a central control unit (CCU, not shown) that is used to control the operation of the metallic impurity collecting apparatus 900.

It is preferred that the loading unit 200, the VPD unit 300, the scanning unit 400, the drying unit 500, and the unloading unit 600 are disposed in an order centering on the transferring robot unit 700. In other words, the loading unit 200, the VPD unit 300, the scanning unit 400, the drying unit 500, and the unloading unit 600 are arcuately disposed centering on the transferring robot unit 700 forming a semicircle-like shape.

Preferably, the shape of the process chamber 100 is substantially a rectangular parallelepiped. The process chamber 100 is preferably airtight and an inner pressure of the process chamber 100 is maintained higher than the outer pressure of the process chamber 100 to thereby prevent contaminated air from flowing into the inner process chamber 100. As a result, it is possible to prevent the semiconductor wafer from being contaminated by alien substances within the air. Thus, the metallic impurity collecting apparatus 900 collects the metallic impurity sample that is only generated in manufacturing process.

The loading unit 200 and the unloading unit 600 are positioned at a location opposite to each other, interposing the transferring robot unit 700 there between. The loading unit 200 and the unloading unit 600 comprise a semiconductor wafer cassette. The semiconductor wafer cassette is capable of handling a plurality of the semiconductor wafers 50.

The VPD unit 300 comprises a loading plate 350, a container 310, and a tank (not shown). The semiconductor wafer 50 is placed on the loading plate 350 that is disposed in the container 310. The container 310 is airtight. The tank contains the HF, and supplies the HF preheated at a predetermined temperature to the container 310. The HF vapors supplied from the tank rapidly decompose the silicon oxide layer of a semiconductor wafer 50. Advantageously, since the HF is set to be preheated at a relatively high temperature from the beginning stage, the HF vapors are evaporated faster than within the methods of the conventional art. The heating temperature of the HF and time period that the semiconductor wafer 50 is exposed to HF in the container 310 can be controlled.

The semiconductor wafer 50 that has undergone the VPD process is transferred to the scanning unit 400 by the transferring robot unit 700.

The scanning unit 400 scans the semiconductor wafer 50 with a scanning solution 80 (see FIG. 5) to collect the metallic impurities from the semiconductor wafer 50.

Thereafter, the semiconductor wafer 50 is transferred from the scanning unit 400 to the drying unit 500 by the transferring robot unit 700.

The drying unit 500 comprises a container 510 and a heating plate 530 disposed in the container 510. The semiconductor wafer is transferred from the scanning unit 400 and placed on the heating plate 530. The container 510 is closed tightly. The heating plate 530 is heated at a predetermined temperature, thereby drying the semiconductor wafer 50.

The drying unit 500 is not required to collect the metallic impurity of the semiconductor wafer 50. However, the drying unit 500 is preferred when the metallic impurity of the semiconductor wafer 50 is analyzed using a total x-ray fluorescent analyzer.

Figure 3:
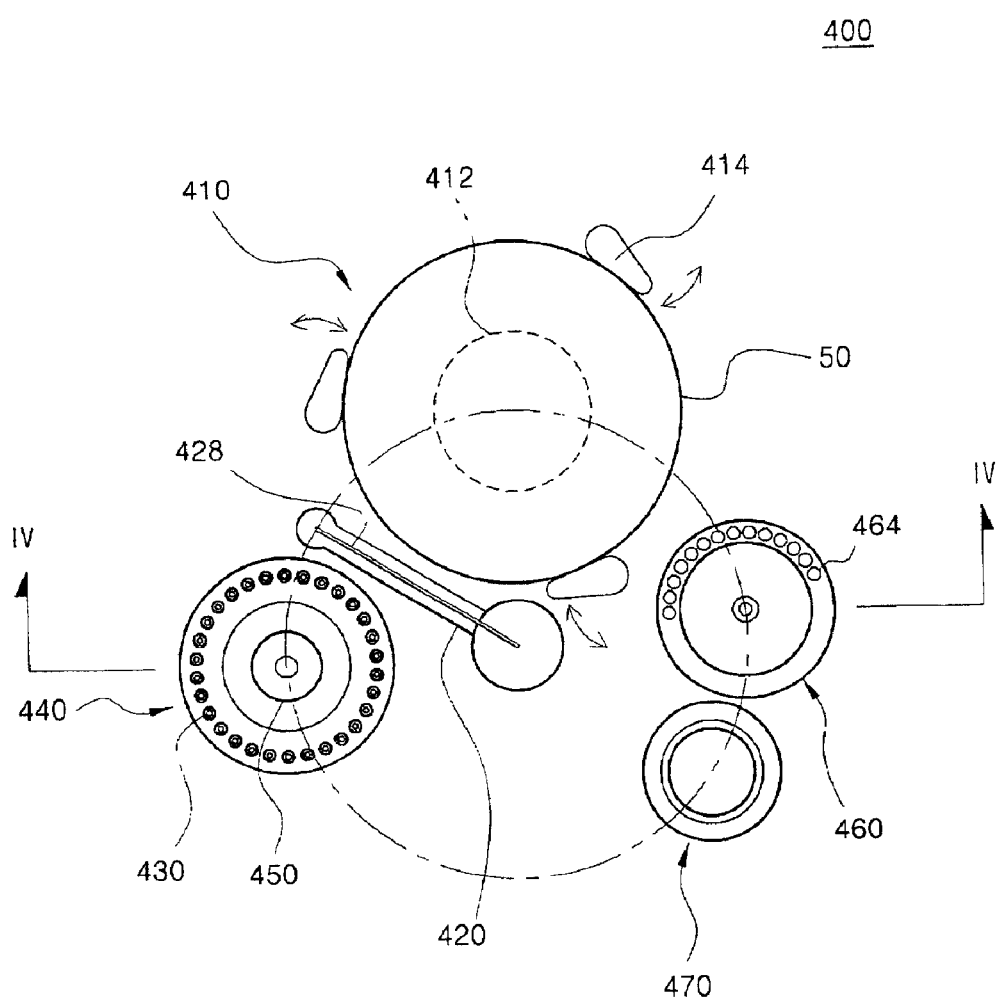
FIG. 3 is a plan view of a scanning unit according to an embodiment of the present invention.
Figure 4:
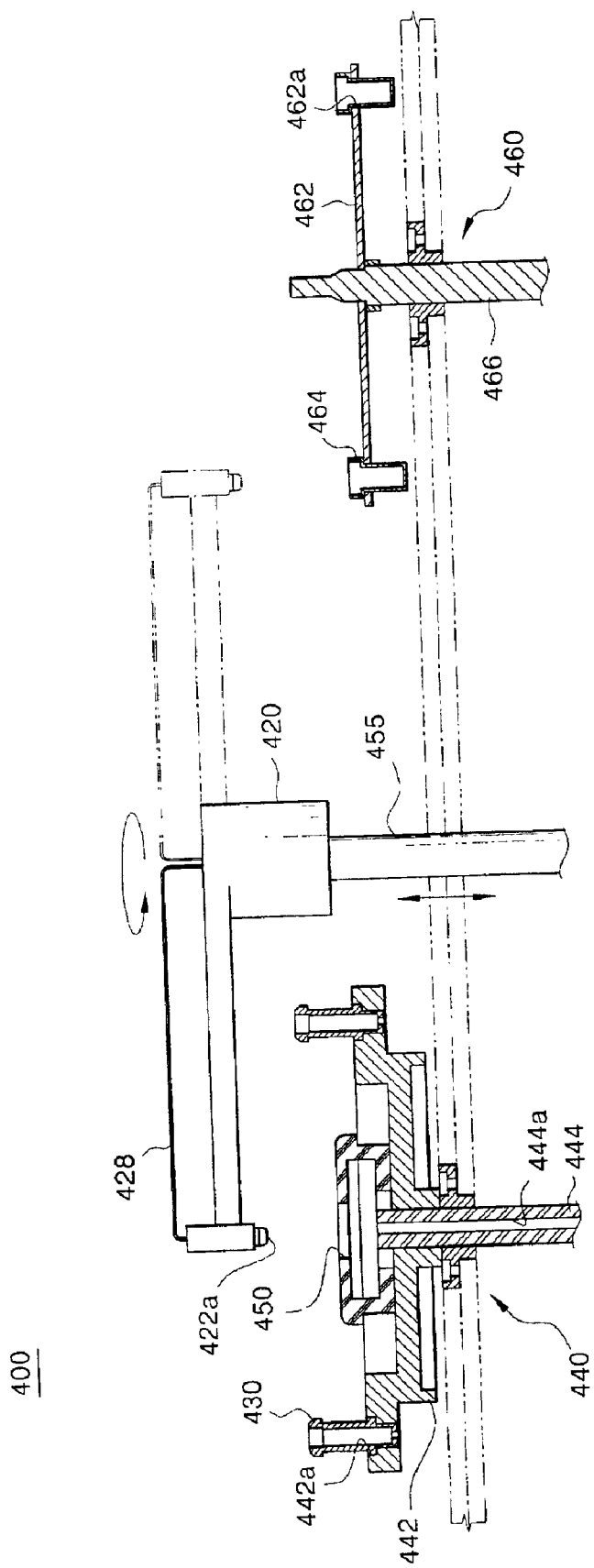
FIG. 4 is a cross—sectional view taken along line IV—IV of FIG. 3.

FIG. 3 is a plan view of the scanning unit 400 according to the preferred embodiment of the present invention. FIG. 4 is a cross-sectional view taken along line IV—IV of FIG. 3.

The scanning unit 400 comprises a wafer aligner 410, a scanning arm 420, a nozzle 430, a nozzle tray 440, a scanning solution bottle 450, a sampling cup tray 460, and a nozzle bottle 470.

The wafer aligner 410 comprises a loading plate 412, a motor (not shown), and an alignment hand 414. When the semiconductor wafer 50 is rested on the loading plate 412, the alignment hands 414 pivotally move in the direction of the arrows as shown, to thereby accurately align the semiconductor wafer 50 with the loading plate 412. Although, three alignment hands 414 are shown in FIG. 3, the invention may comprise any suitable number and arrangement of the alignment hands 414. In FIG. 3, the semiconductor wafer 50 is positioned by the alignment hands 414 to be aligned. Furthermore, it should be appreciated that the invention allows semiconductor wafers 50 comprising different sizes to be aligned with the loading plate 412. The loading plate 412 is rotated by the motor, so that the semiconductor wafer 50 is rotated at a predetermined speed.

Figure 5:
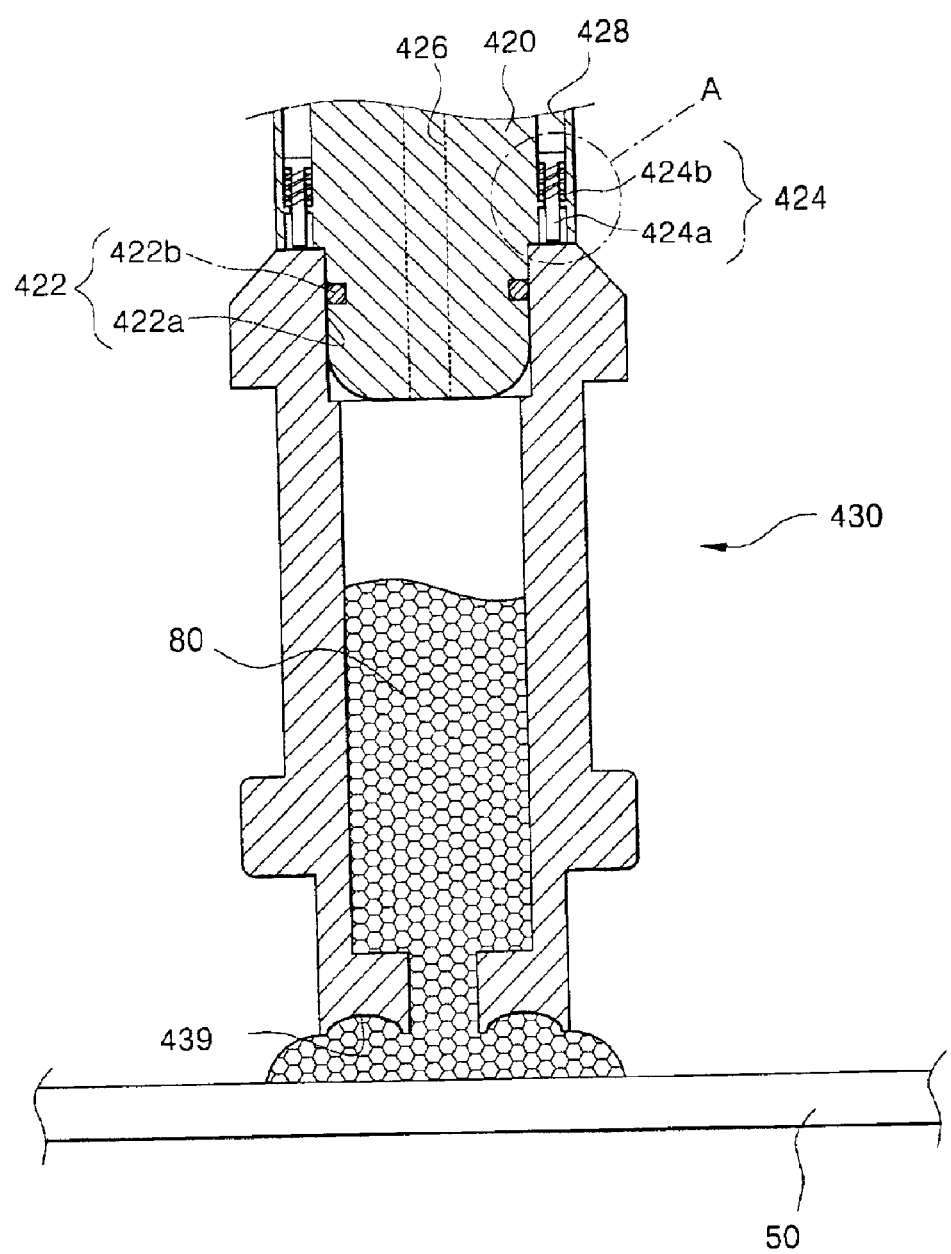
FIG. 5 is a cross—sectional view illustrating a method for coupling a scanning arm and nozzle according to an embodiment of the present invention.
Figure 6:
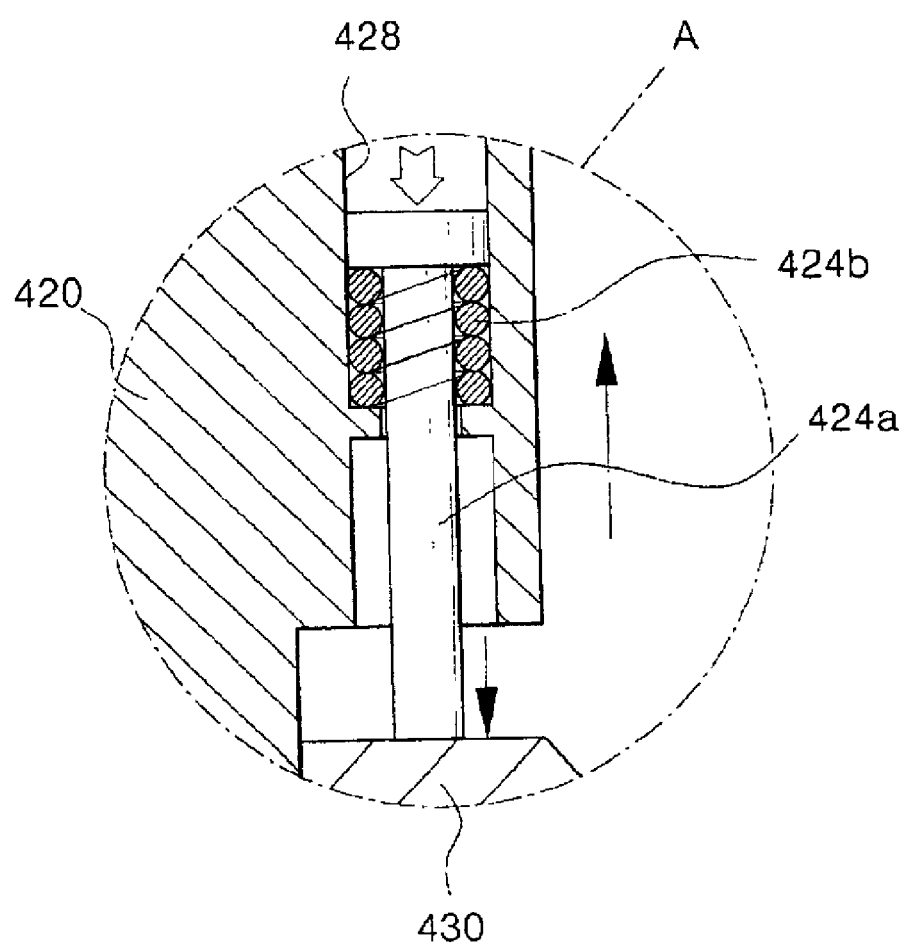
FIG. 6 is an enlarged view illustrating a portion "A" of FIG. 5.

FIG. 5 is a cross-sectional view illustrating a coupling state of the scanning arm 420 and the nozzle 430. FIG. 6 is an enlarged view illustrating a portion "A" of FIG. 5. The scanning arm 420 is coupled to one of a plurality of the nozzles 430 placed on the nozzle tray 440 and scans the semiconductor wafer 50 using the scanning solution 80. The scanning arm 420 can move upward and downward. In addition, the scanning arm is coupled to a rotation shaft 455, which enables the scanning arm to rotate. The scanning arm 420 preferably has an "L" shaped cross-section.

The scanning arm 420 comprises a nozzle-coupling portion 422, a nozzle-removing portion 424, a pumping channel 426, and an air channel 428.

The nozzle-coupling portion 422 comprises a protrusion portion 422*a* and an O-ring 422*b*. The protrusion portion 422*a* protrudes from one end of the scanning arm 420. The O-ring 422*b* is arranged on an outer circumference surface of the protrusion portion 422*a*. The O-ring 422*b* serves to seal the nozzle 430 tightly when the protrusion portion 422*a* is inserted into the nozzle 430 and to secure the nozzle 430 to the scanning arm 420. Preferably, as discussed above, the nozzle-coupling portion 422 is coupled to the nozzle 430 using a clip type arrangement.

The nozzle-removing portion 424 comprises a nozzle removing stock 424*a* and a spring 424*b*. The nozzle removing stock 424*a* removes the nozzle 430 from the scanning arm 420 by pneumatic pressure supplied through the air channel 428. The air channel 428 is connected to a compressor (not shown), and operation of the air channel 428 is controlled by the CCU. The spring 424*b* returns the nozzle removing stock 424*a* back in its former position after detaching the nozzle 430.

The scanning arm 420 comprises a pumping channel 426. The pumping channel 426 is connected to a pump (not shown). The pumping channel is used to create either a pumping or suction force within the nozzle.

When the nozzle 430 is coupled to the scanning arm 420, the pumping channel is used to create a suction force within the nozzle allowing the scanning solution 80 in the scanning solution bottle 450 to be drawn into the nozzle 430. Next, the scanning arm 420 is positioned at a predetermined point over the semiconductor wafer 50. In the nozzle 430, a pumping force is created in the nozzle 430 with enough force so that the scanning solution 80 coheres to the end of the nozzle in the form of a droplet. The scanning arm 420 is then lowered to a position where the scanning solution 80 contacts the semiconductor wafer 50, thereby scanning the semiconductor wafer 50. Once scanning of the semiconductor wafer 50 is complete, the scanning solution 80 is then drawn into the nozzle 430.

Figure 7:
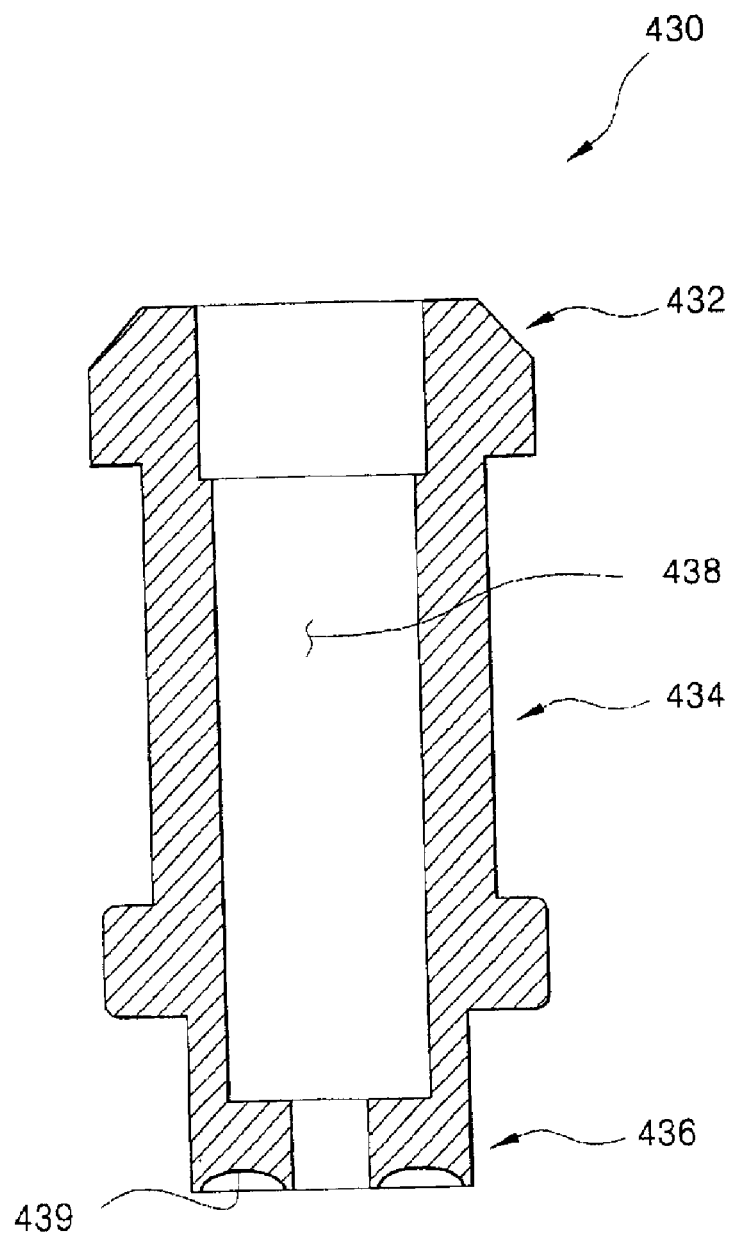
FIG. 7 is a cross-sectional view illustrating a nozzle according to an embodiment of the present invention.

FIG. 7 is a cross-sectional view illustrating the nozzle 430. The nozzle 430 comprises a coupling portion 432, a body portion 434, and an injecting portion 436. A cylindrical shaped hole 438 having a predetermined diameter is formed in the nozzle 430. The drawn scanning solution 80 is reserved in the cylindrical shaped hole 438.

The coupling portion 432 is used for coupling the scanning arm 420 and the nozzle 430 together with the nozzle-coupling portion 422. A portion of the cylindrical shaped hole 438 corresponding to the coupling portion 432 has a diameter large enough to fit the protrusion portion 422*a* of the nozzle-coupling portion 422. As a result, this allows the protrusion portion 422*a* of the nozzle-coupling portion to be inserted into the coupling portion 432, thereby securing the nozzle 430 to the scanning arm 420.

The body portion 434 substantially reserves the scanning solution 80 drawn through the injecting portion 436. A portion of the cylindrical shaped hole 438 corresponding to the body portion 434 has preferably a slightly smaller diameter than that of the corresponding coupling portion 432.

The injecting portion 436 serves to cohere the scanning solution 80 to the nozzle 430. Thus, allowing the semiconductor wafer 50 to be scanned without the scanning solution 80 easily streaming down to the semiconductor wafer 50. A portion of the cylindrical shaped hole 438 corresponding to the injecting portion 436 has a smaller diameter than that of the corresponding body portion 434. A concave portion 439 having a doughnut shape is formed on the bottom surface of the injecting portion 436.

The concave portion 439 increases the contact area between the scanning solution 80 and the nozzle 430 when the scanning solution 80 is released through the injecting portion 436. Therefore, the surface tension of the cohered scanning solution 80 increases so that the scanning solution 80 does not easily stream down onto the semiconductor wafer 50.

The nozzle tray 440, shown in FIG. 4, comprises a disc plate 442. The disc plate 442 includes a plurality of nozzle reception grooves 442*a* formed on a peripheral region thereof. Each of the nozzle reception grooves 442*a* accepts a corresponding nozzle 430. The nozzle tray 440 is coupled to a rotation shaft 444, which allows the nozzle tray 440 to rotate. The rotation shaft 444 has a scanning solution channel 444*a* formed therein. The scanning solution 80 is supplied to the scanning solution bottle 450 through the scanning solution channel 444*a*.

The scanning solution bottle 450 having the scanning solution 80 therein is preferably arranged at a central portion of the nozzle tray 440. The scanning solution 80 has enough cohesion (cohesive property) to absorb the metallic impurity of the semiconductor wafer 50. Preferably, the scanning solution 80 comprises a composition of $H_2O$, $H_2O_2$, and HF in a ratio of about 95%:4%:1%, respectively.

The sampling cup tray 460 comprises a disc plate 462. The disc plate 462 comprises a plurality of sampling cup reception holes 462a formed on a peripheral region thereof (of the disc plate 462). Each of a plurality of the sampling cup reception holes 462a accepts a corresponding sampling cup 464. The scanning solution 80 including the metallic impurity is placed into the sampling cup 464. A rotation shaft 466 is coupled to the sampling cup tray 460, which allows the sampling cup tray 460 to rotate.

The nozzle bottle 470 has a cylindrical shape. After the sample of the metallic impurity is collected and placed into a sampling cup 464, the nozzle 430, which is used to collect the metallic impurity, is decoupled from the scanning arm 420 and discarded into the nozzle bottle 470.

The loading plate 412, the nozzle tray 440, the scanning solution bottle 450, the sampling cup tray 460, and the nozzle bottle 470 are arranged so that the scanning arm 420 may rotate to perform corresponding operations. For example, the scanning solution bottle 450 is arranged at a location corresponding to where the nozzle 430 is coupled to the scanning arm 420. This allows the scanning arm 420 to rotate to the scanning solution bottle 450 and to draw the scanning solution 80. In addition, once the sample of the metallic impurity is collected into the sample cup 464, after the nozzle bottle 470 is arranged so that the nozzle 430 may be removed from the scanning arm and discarded into the nozzle bottle 470.

Preferably as depicted in FIG. 3., an imaginary line (i.e., one dot line) connecting respective central points of the loading plate 412, the nozzle tray 440, the sampling cup tray 460, and the nozzle bottle 470 forms a circle.

The transferring robot unit 700 has a robot arm shape, and is pivotally rotatable. Preferably, the transferring robot unit 700 transfers a semiconductor wafer 50 to the VPD unit 300, the scanning unit 400, the drying unit 500 and the unloading unit 600 for a corresponding process.

Hereinafter, a method according to an embodiment of the invention for collecting the impurity of the semiconductor wafer using the metallic impurity collecting apparatus 900 is described.

Initially, one of the manufactured semiconductor wafers 50 manufactured is selected and loaded on the loading unit 200 in the process chamber 100. The process chamber 100 is tightly shut.

The transferring robot unit 700 transfers the semiconductor wafer 50 from the loading unit 200 to the VPD unit 300. The semiconductor wafer 50 is placed on the loading plate 350 in the container 310, and the container 310 is shut. The silicon oxide layer is decomposed from the semiconductor wafer 50 by the HF vapors. The transferring robot unit 700 transfers the semiconductor wafer 50 from the VPD unit 300 to the scanning unit 400. The semiconductor wafer 50 is aligned and placed on the loading plate 412 of the wafer aligner 410.

At the same time, the scanning arm 420 rotates to the nozzle tray 440 moves downward to couple to one of the nozzles 430 in the nozzle tray 440. The scanning arm 420 coupled to the nozzle 430 moves up and rotates to the scanning solution bottle 450. The scanning arm 420 positioned over the scanning solution bottle 450 moves downward to draw the scanning solution 80 using a suction source. Here, a preferable amount of the scanning solution 80 to drawn is at a level just below the nozzle-coupling portion 422 of the scanning arm 420, whereby an air gap is formed between the drawn scanning solution 80 and the bottom surface of the protrusion portion 422a. This is preferred because the nozzle-coupling portion 422 could be contaminated by the metallic impurity absorbed in the scanning solution 80 in the subsequent collecting process, if the drawn scanning solution 80 contacts the nozzle-coupling portion 422. Indeed, a then the contaminated nozzle-coupling portion 422 can affect the next metallic impurity collecting process.

Thereafter, the scanning arm 420 rotates and is positioned over a portion of the semiconductor wafer 50 to be scanned.

The scanning arm 450 moves downward to scan the semiconductor wafer 50 using the scanning solution 80. At the same time, the metallic impurities of the semiconductor wafer 50 are absorbed into the scanning solution 80.

More specifically, the scanning solution 80 is forced through the injecting portion 436 by using a appropriate pumping force supplied via the pumping channel 426 to form a droplet of scanning solution that coheres to the injection portion 436. The scanning solution 80 droplet coheres to the injecting portion 436 rest between the injection portion 436 and the semiconductor wafer 50 due to an increase in surface tension created by the concave portion 439. At this moment, the semiconductor wafer 50 rotates in a predetermined direction by the motor of the wafer aligner 410, whereby the semiconductor wafer 50 is scanned by the scanning solution 80. At this moment, the scanning solution 80 absorbs the metallic impurities of the semiconductor wafer 50 while scanning the semiconductor wafer 50. The amount of the scanning solution exhausted depends on a process and a size of the semiconductor wafer 50. Preferably, the amount of scanning solution released forms a droplet that coheres to the injecting portion 436. The scanning arm 420 is then lowered so that the scanning solution 80 is placed onto the semiconductor wafer 50, and the semiconductor wafer 50 is rotated at a speed that allows the scanning solution droplet to absorb the metallic impurities on the semiconductor wafer 50.

Figure 8:
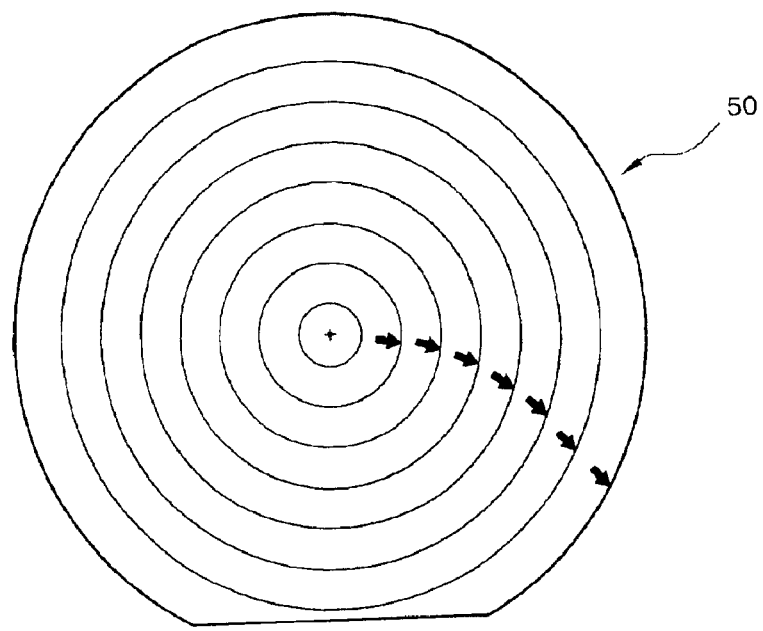
FIG. 8 is a diagram to illustrate a scanning method according to an embodiment of the present invention.
Figure 9:
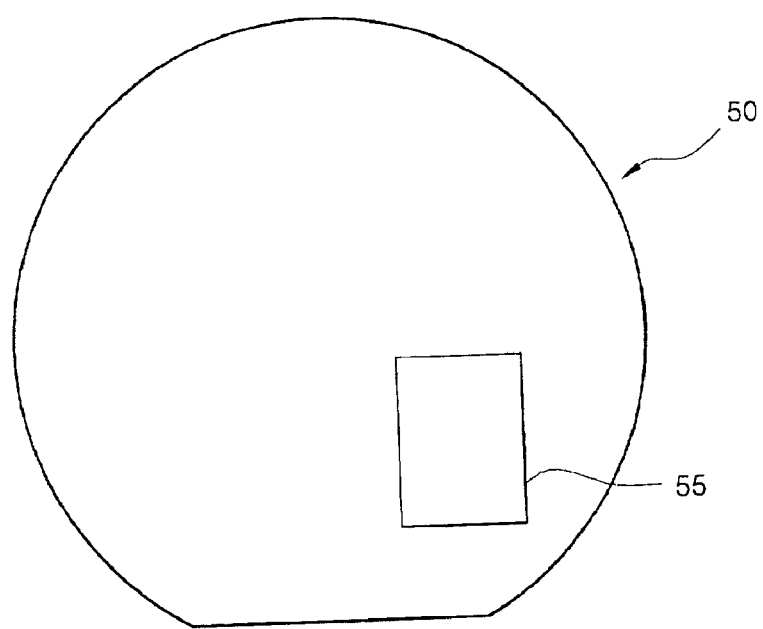
FIG. 9 is a diagram to illustrate a scanning method according to an embodiment of the present invention.

FIGS. 8 and 9 are diagrams illustrating exemplary scanning methods according to the present invention. For example, the entire surface of the semiconductor wafer 50 can be scanned (as shown in FIG. 8), whereas a portion of the semiconductor wafer 50 can be scanned (as shown in FIG. 9). In the case that the entire surface of the semiconductor wafer 50 is scanned, whenever the semiconductor wafer 50 takes one turn, the nozzle 430 coupled to the scanning arm 420 moves step by step outwardly or inwardly not to overlap or rescan a previously scanned portion of the wafer. Alternatively, in the case that a part of the semiconductor wafer 50 is scanned, the scanning arm 420 is operated to scan a selected local part 55.

Subsequently, a rotation of the semiconductor wafer 50 is stopped, and the scanning solution droplet containing the metallic impurities is drawn into the nozzle 430 by a suction force supplied via the pumping channel 426 from the pump so as to prevent the scanning solution from dropping down during the movement of the scanning arm 420.

At this point, a subsequent process depends on an analysis method. For the sake of simplicity, two analyses are exemplarily described.

Firstly, in case that the atomic absorption spectroscopy is employed, the scanning arm 420 rotates to the sampling cup tray 460 and exhausts the collected sample of the metallic impurities into the sampling cup 464 using a pump force. The scanning arm 420 rotates to the nozzle bottle 470, and detaches the nozzle 430 therefrom and puts the detached nozzle 430 in the nozzle bottle 470 by the nozzle-removing portion 424.

The transferring robot unit 700 transfers the semiconductor wafer 50 to the unloading unit 600 and simultaneously unloads it outside the process chamber 100, thereby completing a process of collecting the metallic impurities of semiconductor wafer 50.

Secondly, in case that a total x-ray fluorescent analyzer is employed, the scanning arm 420 exhausts the collected sample of the metallic impurities in center of the semiconductor wafer 50 using a pump force. The scanning arm 420 rotates to the nozzle bottle 470, and detaches the nozzle 430 therefrom and puts the detached nozzle 430 in the nozzle bottle 470 by the nozzle-removing portion 424.

The transferring robot unit 700 transfers the semiconductor wafer 50 to the heating plate 530 of the dry unit 500. The semiconductor wafer 50 is dried and transferred to the unloading unit 600, thereby completing the process of collecting the metallic impurities of (on) a semiconductor wafer 50.

As described herein before, according to the preferred embodiment of the present invention, a process of collecting the metallic impurity of the semiconductor wafer is automatically performed, and thus a highly reliable analysis data can be obtained. In addition, a process of collecting the metallic impurity of the semiconductor wafer is performed in an airtight process chamber, and thus it possible to prevent the metallic impurity sample of the semiconductor wafer from being contaminated by the alien substances in the air, which leads to a highly reliable analysis data.

Further, a plurality of nozzles are used for collecting the metallic impurity of the semiconductor wafers, and an amount of the scanning solution drawn is at a level in the cylindrical shape hole 438 just below the nozzle coupling portion of the scanning arm, and thus highly reliable analysis data can be obtained.

Furthermore, the nozzle has the concave portion in the shape of a doughnut, which forms the scanning solution into a droplet; As a result, the metallic impurity of the semiconductor wafer can be collected efficiently.

While the invention has been particularly shown and described with reference to preferred embodiments thereof, it will be understood by those skilled in the art that the foregoing and other changes in form and details may be made therein without departing from the spirit and scope of the invention.

What is claimed is:

1. An apparatus for collecting metallic impurities on a semiconductor wafer, comprising:
   a process chamber comprising a loading unit for loading the semiconductor wafer and an unloading unit for unloading the semiconductor wafer;
   a vapor phase decomposition unit disposed in the process chamber for decomposing a silicon oxide layer on the semiconductor wafer; and
   a scanning unit disposed in the process chamber for scanning the semiconductor wafer to collect metallic impurities, the scanning unit comprising:
      a scanning solution bottle for storing scanning solution that is used for absorbing metallic impurities on the semiconductor wafer;
      a scanning arm that moves in a downward, upward, and rotational motion; and
      a nozzle for coupling to the scanning arm for drawing in scanning solution from the scanning solution bottle, and for forming a droplet of scanning solution that coheres to the nozzle when scanning the semiconductor wafer to collect metallic impurities.

2. The apparatus of claim 1, wherein the process chamber further comprises a drying unit for drying the semiconductor wafer.

3. The apparatus of claim 1, wherein the nozzle comprises:
   a cylindrical hole storing the scanning solution;
   a coupling portion for coupling to the scanning arm; and
   an injecting portion for contacting the scanning solution to the semiconductor wafer, wherein a bottom surface of the injecting portion comprises a concave-shaped portion.

4. The apparatus of claim 1, wherein the scanning arm comprises a nozzle-coupling portion that couples to the coupling portion of the nozzle.

5. The apparatus of claim 4, wherein the scanning arm further comprises:
   a nozzle-removing portion; and
   an air channel for supplying pneumatic pressure to the nozzle removing portion to decouple the nozzle from the nozzle-coupling portion of the scanning arm.

6. The apparatus of claim 1, wherein the scanning unit comprises a sampling cup tray for holding a plurality of sample cups, and wherein the scanning arm comprises a pumping channel for supplying one of a pumping and suction force to the nozzle, such that the scanning solution can be drawn into the nozzle using the suction force, or contacted to the semiconductor wafer or emptied into a sampling cup using the pumping force.

7. The apparatus of claim 1, wherein the scanning unit further comprises:
   a wafer aligner comprising an alignment hand and a loading plate, wherein the semiconductor wafer is aligned with the loading plate by the alignment hand;
   a nozzle tray comprising a plurality of nozzle reception grooves for accepting a plurality of nozzles;
   a sampling cup tray comprising a plurality of sampling cup reception holes for accepting a plurality of sampling cups, wherein the collected metallic impurities are placed in a sampling cup; and
   a nozzle bottle for disposing used nozzles therein.

8. The apparatus of claim 1, wherein the scanning solution bottle is disposed on a central portion of a nozzle tray.

9. The apparatus of claim 7, wherein the loading plate is rotated by a motor.

10. The apparatus of claim 1, wherein the scanning solution comprises $H_2O$, $H_2O_2$, and HF.

11. The apparatus of claim 1, wherein the scanning solution comprises $H_2O$, $H_2O_2$ and HF in a ratio of about 95:4:1, respectively.

12. An automated method for collecting metallic impurities on a semiconductor wafer, comprising the steps of:
   decomposing a silicon oxide layer on a semiconductor wafer using hydrofluoric acid vapors;
   drawing scanning solution into a nozzle and forming a droplet of scanning solution that coheres to the nozzle; and
   scanning the semiconductor wafer by contacting the droplet of scanning solution to the semiconductor wafer to collect metallic impurities.

13. The method of claim 12, wherein the hydrofluoric acid is preheated.

14. The method of claim 12, further comprising the steps of:
coupling the nozzle to a nozzle-coupling portion of a scanning arm, and
drawing an amount of scanning solution into the nozzle through an injection portion of the nozzle so that the level of scanning solution in the nozzle is below the nozzle-coupling portion of the scanning arm.

15. The method of claim 12, wherein the step of scanning comprises positioning the nozzle at a predetermined point using a scanning arm and rotating a loading plate holding the semiconductor wafer.

16. The method of claim 15, wherein the step of scanning further comprises:
holding the nozzle at the predetermined point until the semiconductor wafer makes one rotation; and
changing the predetermined point one of inwardly and outwardly such that there is no overlap of a previously scanned portion of the semiconductor wafer.

17. The method of claim 12, wherein the scanning solution comprises $H_2O$, $H2O_2$, and HF.

18. The method of claim 12, wherein the scanning solution comprises $H_2O$, $H_2O_2$, and HF in a ratio of about 95:4:1, respectively.

19. An automated method for collecting metallic impurities on a semiconductor wafer, comprising the steps of:
loading a semiconductor wafer in a loading unit;
transferring the semiconductor wafer to a vapor phase decomposition device;
decomposing a silicon oxide layer on the semiconductor wafer using hydrofluoric acid vapors in the vapor phase decomposition device;
transferring the semiconductor wafer to a scanning unit and coupling a nozzle to a scanning arm;
drawing scanning solution into the nozzle and forming a droplet of scanning solution on the nozzle;
contacting the droplet of scanning solution to the semiconductor wafer to scan the semiconductor wafer and absorb metallic impurities into the scanning solution; and
drawing the droplet of scanning solution having metallic impurities back into the nozzle and disposing the scanning solution from the nozzle into a sampling cup or back into the semiconductor wafer.

20. The method of claim 19, further comprising the steps of: transferring the nozzle to a nozzle bottle;
decoulping the nozzle into the nozzle bottle; and
transferring the semiconductor wafer to a unloading unit.

* * * * *